(12) United States Patent
Haberbosch (10) Patent No.: US 7,785,614 B2
(45) Date of Patent: *Aug. 31, 2010

(54) 3-DEAZAADENOSINE PREVENTS ATHEROSCLEROSIS AND GRAFT VASCULOPATHY

(75) Inventor: Werner Haberbosch, Gießen (DE)

(73) Assignee: Kerckhoff-Klinik Gesellschaft Mit Beschränkter Haftung, Bad Nauheim (DE)

( * ) Notice: Subject to any disclaimer, the term of this patent is extended or adjusted under 35 U.S.C. 154(b) by 1126 days.

This patent is subject to a terminal disclaimer.

(21) Appl. No.: 10/655,225

(22) Filed: Sep. 4, 2003

(65) Prior Publication Data

US 2004/0106563 A1    Jun. 3, 2004

(51) Int. Cl.
*A61F 2/82* (2006.01)
(52) U.S. Cl. .................................................. 424/423
(58) Field of Classification Search ............... 424/423
See application file for complete search history.

(56) References Cited

U.S. PATENT DOCUMENTS 4,322,411 A * 3/1982 Vinegar et al. ............... 514/46
5,234,456 A * 8/1993 Silvestrini .................. 623/1.2
6,693,088 B1 * 2/2004 Haberbosch ................ 514/46
2003/0203976 A1 * 10/2003 Hunter et al. ............. 514/772.3

OTHER PUBLICATIONS

Dzau et al, "Vascular Proliferation and Atherosclerosis: NEw Perspectives and Therapeutic Strategies", Nat Med. 2002; 8:1249-1256.*
Dzau et al, "vascular Proliferation and Atherosclerosis: New Perspectives and Therapeutic Strategies", Nat MEd 2002; 8: 1249-1256.*
Mizuno et al Nucleotides. III Syntheses of deazaadenosine cyclic 3',5'-phosphates and related nucleotides of biological interest, Fac. Pharm. Sci., Hokkaido UNiv., Sapporo, Japan, Chemical and Pharmaceutical Bulletin (1975), 23(8),1664-70.*
Ikehara, Deazaadenosine Polymers, Mitsubishi Chemicasl Industries Co. Ltd, Japan, Japan Kokai Tokkyo Koho, 6 pp.*

* cited by examiner

Primary Examiner—Carlos A Azpuru
(74) Attorney, Agent, or Firm—Fulbright & Jaworski L.L.P.

(57) ABSTRACT

The invention relates to the use of 3-deazaadenosine and analogs thereof for the manufacture of a medicament against vascular diseases or graft rejection.

15 Claims, 8 Drawing Sheets

3-DEAZAADENOSINE PREVENTS ATHEROSCLEROSIS AND GRAFT VASCULOPATHY

This application claims priority from U.S. Ser. No. 09/786,672 filed Apr. 6, 2001, allowed which is a §371 from PCT/EP99/06462 filed Sep. 2, 1999

The invention relates to the use of 3-deazaadenosine ($c^3$Ado) for the preparation of a medicament against vascular diseases or graft rejection, especially atherosclerosis and graft vasculopathy.

Adhesion of leukocytes to the endothelial cell layer and their subsequent migration into the vascular wall are believed to play a key role during the development of atherosclerotic lesions. Monocytes/macrophages and lymphocytes, for example, are ubiquitous at all stages of atherosclerotic plaque development and propagate the local inflammatory process. Furthermore, lipid-laden macrophages accumulate within the plaque, thereby leading to instability with consequent rupture, thrombosis and acute vessel closure (1-3).

It has been widely appreciated that the inhibition of leukocyte adhesion and migration may have protective effects on plaque development (4-6). Cellular adhesion and migration are mediated by various molecules of the selectin, integrin, and immunoglobulin superfamily, such as the adhesion molecules vascular cell adhesion molecule-1 (VCAM-1) and intercellular adhesion molecule-1 (ICAM-1). Previous studies have demonstrated increased expression of VCAM-1 and ICAM-1 on the surface of endothelial and vascular smooth muscle cells of human plaques and in experimental models of atherosclerosis (7-13). A recent study on C57/BL6 mice with homozygous mutations for various adhesion molecules indicated that endothelial adhesion molecules are directly involved in the pathogenesis of atherosclerosis (14).

Adhesion of leukocytes to the vascular endothelium is also an early step in graft rejection, leading to the migration of inflammatory cells into underlying tissues. Endothelial cells contribute to adhesion by expressing several inducible cell surface molecules that bind various inflammatory cells. Together with MHC molecules, the adhesion molecules have an important role in T-cell activation for inflammatory cell adhesion to activated endothelial cells at least three separate receptor/ligand pairs are involved: ICAM-1/LFA-1, VCAM-1/VLA-4, and E-selectin/sialyl Lewis X, and/or related carbohydrates on leukocytes.

Current models propose that members of the selectin gene family (E-, P-, and L-selectin) mediate the initial adhesive interactions, including leukocyte rolling, and that subsequent firm adhesion and diapedesis require activation-dependent engagement of integrins with their endothelial ligands and PECAM-1, respectively.

Several previous studies showed that VCAM-1, ICAM-1, P-selectin, and LFA-1 are extensively expressed on endothelial cells in rat heart allograft atherosclerosis. Treatment of animals with antibodies to VCAM-1, VLA-4, ICAM-1 and LFA-1 induced immunosuppression and inhibited graft atherosclerosis. Also the administration of ICAM-1 antisense oligonucleotides led to immunosuppression. In contrast, in ICAM-deficient mice no prolongation of cardiac allograft survival could be detected, indicating that this protein is not alone responsible for the induction of rejection or graft vasculopathy.

3-Deazaadenosine ($c^3$Ado), a structural analog of adenosine, is an anti-inflammatory drug that has been shown to inhibit monocyte chemotaxis and phagocytosis (15-18). Furthermore, there are data revealing that this adenosine analog reduces tumor necrosis factor-α-induced macrophage adhesion to endothelial cells in vitro via the selective inhibition of ICAM-1 synthesis (19). The underlying molecular mechanisms have not yet been fully clarified. $c^3$Ado inhibits cellular methylation of membrane phospholipids and suppresses adenosylhomocysteine hydrolase (20,21). However, it has been suggested that the biological actions of $c^3$Ado are independent of these mechanisms (21-24).

Because of its anti-inflammatory properties, $c^3$Ado has been studied in a clinical trial in patients with rheumatoid arthritis (19,25), and this drug will be tested in humans for its in vitro antiviral (HIV) activity (26). The drug has never been tested in animal models of vascular disease.

Surprisingly, it was found that $c^3$Ado inhibits in vivo leukocyte adhesion and concomitant formation of atherosclerotic lesions via inhibition of the expression of endothelial cell adhesion molecules, such as VCAM-1 and ICAM-1, as demonstrated in female C57/BL6 mice. These animals are reproducibly susceptible to fatty lesion formation which closely resembles early atherosclerotic plaques detected in humans (27-31).

Further, it was found that $c^3$Ado inhibits graft rejection and graft atherosclerosis in transplanted hearts.

An aspect of the present invention is the use of 3-deazaadenosine or analogs thereof for the manufacture of a medicament for the prevention and/or treatment of vascular diseases or graft rejection.

A further aspect of the present invention is the use of 3-deazaadenosine and analogs thereof for the manufacture of a medicament for the prevention and/or treatment of diseases associated with the expression of adhesion molecules ICAM-1 and VCAM-1 in endothelial cells.

According to the present invention 3-deazaadenosine and analogs thereof can be used. Examples of such analogs are salts of 3-deazaadenosine and precursors of 3-deazaadenosine which can be degraded in the body under physiological conditions to give 3-deazaadenosine, e.g. 3-deazaadenosine phosphates. Further examples of analogs are deazanucleosides such as 3-deazaadenosine-3'-monophosphoric acid, 3-deazaadenosine-3',5'-cyclophosphate and 3-deazaadenosine-5'-diphosphoric acid and salts and precursors thereof, respectively.

3-Deazaadenosine and analogs thereof are capable of preventing or delaying the occurrence of atherosclerosis. They prevent the appearance of fatty streak formation and all other stages of atherosclerotic plaque development in the intima of arterial blood vessels via inhibition of the expression of adhesion molecules in vascular endothelial cells. This leads to a reduction of adhesion and consecutive infiltration of monocytes into the subendothelial layer. Therefore the inhibition of the endothelial expression of VCAM-1 and ICAM-1 is the key mechanism, by which $c^3$Ado inhibits atherosclerosis.

By the same mechanism $c^3$Ado and analogs inhibit graft atherosclerosis in transplanted organs. Examples of transplanted organs are hearts, kidneys, livers, lung etc. The administration of 3-deazaadenosine and analogs thereof leads to reduced occlusion of blood vessels, particularly arterial blood vessels in transplanted organs. Furthermore, reduction of rejection of transplanted organs, for example, reduction of rejection of transplanted hearts is achieved.

Thus, $c^3$Ado is suitable for the prevention and/or treatment of transplant vasculopathy.

Further preferred indications of 3-deazaadenosine and analogs thereof are prevention of rejection in xenotransplantation, prevention of restenosis after coronary interventions, especially after stent-implantation. Restenosis in stents (in-stent restenosis) can be prevented by coating the stent to be used with 3-deazaadenosine. The combination of covalent binding of 3-deazaadenosine to stents is effective for the prevention of restenosis. Further preferred indications are prevention of reperfusion injuries, e.g. in the heart or in the lung, treatment and prevention of infectious and inflammatory coronary syndromes, prevention and treatment of dilated cardiomyopathy, prevention and treatment of viral myocarditis and prevention and treatment of infections by parasites such as Malaria tropica.

Another preferred indication is the use of 3-deazaadenosine and analogs thereof for reducing the level of homocysteine.

3-Deazaadenosine and analogs thereof can be used individually or in combination with other medicaments. When treating vascular diseases, for example, combination with cholesterol-reducing agents is conceivable. To prevent graft rejection 3-deazaadenosine and analogs thereof can be used in combination with immunosuppressive medicaments, e.g. cyclosporine. 3-Deazaadenosine and analogs thereof also can be combined with azathioprine, cortisone, rapamycine, tacrolimus and other immunosuppressive drugs.

The medicament can be administered any way, e.g. parenterally by means of injection or orally. Oral administration, e.g. in the form of tablets, capsules etc. is preferred.

The dose administered depends on the kind and severity of the disease. Normally, the dose ranges between 0.1 to 500 mg/kg body weight per day, preferably between 1 to 200 mg/kg body weight per day. Administration can be effected over a short period of one or more days. However, administration is usually effected over a period of at least one week. The dose can be varied during the administration period, if necessary.

A further aspect of the invention is a method of treating or preventing vascular diseases or graft rejection, comprising administering to a subject in need thereof, e.g. a human, an efficient amount of 3-deazaadenosine or an analog thereof.

Yet a further aspect of the invention is a method of treating or preventing diseases associated with expression of adhesion molecules ICAM-1 and VCAM-1 in endothelial cells comprising administering to a subject in need thereof, e.g. a human, an efficient amount of 3-deazaadenosine or an analog thereof.

The invention is explained in more detail by the following Figures and Examples.

FIGURE LEGENDS

FIGS. 3(A-C) Corresponding light micrographs of cross sections of the aortic wall (200 μm cranial to aortic valve) taken from female C57BL/6J mice. (A) Group 2 fed with the atherogenic diet for 9 weeks demonstrates proliferation of the aortic intima. In contrast the neointima was absent in mice treated with 3-deazaadenosine (B). (C) Controls. Oil red O and hemalaun. A-C: original magnification×40; bar=10 μm.

FIGS. 4(A-F) Cross sections of the ascending aorta with strong ICAM-1-positive (A) and strong VCAM-1-positive (B) endothelial cells in mice on atherogenic diet. In mice treated with 3-deazaadenosine (C+D) as well as in controls (E+F), no endothelial expression of ICAM-1 and VCAM-1 in the aorta was detected. ICAM-1 and VCAM-1 staining with monoclonal rat anti-mouse antibodies using the APAAP method and counterstaining with hemalaun. A-F: original magnification×100; bar=5 μm.

EXAMPLE 1

Prevention of Atherosclerosis 1.1 Materials and Methods 1.1.1 Animals, Atherogenic Diet and Experimental Design Six to eight week old female C57BL/J6 mice (Charles Rivers Wiga, Sulzfeld, Germany) with an average body weight of 20 g were randomly divided into three groups:

Group 1: control animals (n=9) maintained on a normal mouse diet (Altromin, Standard Diet; Lage, Germany).

Group 2: nine animals receiving an atherogenic diet based on normal mouse chow but differing in total fat content (10% vs. 5%), protein content (15.4% vs. 22%) and cholesterol content (1% vs. 0%). The total energy was 3790 vs. 3000 kcal/kg.

Group 3: nine animals on an atherogenic diet as described above, and 3-deazaadenosine ($c^3$Ado) (Southern Research, Birmingham, Ala., USA) mixed into the food at a final concentration of 0.04 mg/g, according to a daily oral dose of 10 mg/kg $c^3$Ado per animal.

The average intake of food for each animal was 5.2 g per day. Food and water were replenished every 2 days, and the volumes consumed for each cage were recorded. The mice were kept in accordance with standard animal care requirements and were maintained on a 12 hour light-dark cycle with autoclaved water in a temperature-controlled environment. All animals remained healthy during the experimental period. After 9 weeks, mice were sacrificed by inhalation of trichlormethane. The heart and the ascending aorta were removed and rinsed with PBS DULBECCO'S (Life Technologies, Paisley, Scotland.) The lower half of the heart was transected along a line between the tips of the atria to obtain a base for the emerging ascending aorta. This procedure allowed an exact vertical embedding of the aorta in Tissue-Tek (Miles, USA) for optimal plane cross sections. The sections were frozen in liquid nitrogen and stored at −80° C. until further study.

1.1.2 Quantification of Atherosclerotic Lesions and Neointimal Proliferation

A modification of the method described by Paigen et al. (29) was used to evaluate aortic lesion formation. The frozen tissue blocks were placed on a cryotome, and 8 μm serial sections of the ascending aorta were collected on coated glass slides until we were able to locate the most cranial portion of the aortic sinus by examining unstained sections. Once this section (No. 1) was identified, the cranial 35 sections, covering 280 μm of the ascending aorta, were placed on separate slides for further evaluation. Every fifth section of the first 280 μm of the ascending aorta was stained with oil red O (Riedel de Haen, Germany) and counterstained with hemalaun (Merck, Darmstadt, Germany) and elastic van Gieson (Chroma-Gesellschaft, Schmid GmbH, Köngen, Germany). Lesion area as well as intimal and medial area were blindly determined using a video-computer aided microscopy planimetry system (Zeiss, Oberkochen, Germany; Video Camera 3 CCD, Sony; 40× lens magnification; IBAS-2 with IBAS Version 2.0 Standard, Kontron, München, Germany).

The number of lesions was counted as described previously by reviewing every fifth section. This procedure resulted in 40 μm between each evaluated section. The number of lesions in each cross section was also counted. Size of the lesions was determined as length of lesion along the luminal aortic perimeter which was related to the total luminal aortic perimeter in the section.

The extent of neointimal proliferation was quantified by measuring the area ($\mu m^2$) of the neointima and the media in each ascending aorta from 3 sections (No. 10, 20 and 30). In each section four sectors (at 0°, 90°, 180° and 270°) of the vessel wall were analyzed in a defined window of 63 μm×63 μm to measure neointimal area enclosed by the endothelial layer and internal elastic lamina and external elastic lamina. Ratio of neointimal to medial are ratio (NI/M) was averaged for each animal.

1.1.3 Immunohistochemical Analysis

Serial cryostate sections (8 μm) from the following 3 parts of the ascending aorta were chosen: 8-32 μm, 120-144 μm and 240-264 μm distal to the aortic sinus. The frozen sections were fixed in ice-cold acetone and dried for 10 minutes. Sections were then incubated for 10 minutes in a 1:1000 dilution of mouse serum (Sigma, St. Louis, Mo., USA). After rinsing with RPMI 1640 (Life Technologies, Paisley, Scotland), the sections were incubated for 40 minutes at room temperature with a 1:100 dilution of a monoclonal rat anti-mouse antibody against ICAM-1 (CF54) or VCAM-1 (CD106, Dianova GmbH, Hamburg, Germany). Detection of monocytes/macrophages was performed using monoclonal rat anti-mouse antibody CD11b (MAC-1) (Serotec Ltd., Oxford, England).

After additional washing steps with TRIS buffer (USB, Cleveland, Ohio, USA) and incubation with a secondary antibody (AffiniPureMouse anti-rat IgG, Dianova, Germany) (1:400) for 10 minutes, followed by incubation with a linking antibody (Dualsystem-Brückenantikörper; Dianova, Hamburg, Germany) (1:600) for 10 minutes, the sections were incubated with an alkaline phosphatase anti-alkaline phosphatase complex (APAPP) (1:50; Dianova, Hamburg, Germany) for 30 minutes. The development of the sections was performed in neufuchsin developer solution. Sections were finally counterstained with hemalaun (Merck, Darmstadt, Germany) for 10 seconds. Control sections were treated with linking secondary antibody and APAAP complex only.

1.1.4 Quantification of Immunohistochemical Staining

The intensity of staining with ICAM-1 and VCAM-1 was scored from 1 to 4 as follows: score 1=no staining, score 2=weak staining, score 3=moderate staining and score 4=strong staining of the vascular cells. The number of CD11b-positive cells was counted in each section, and the localization of the cells was classified as adherent to the wall, or localized in the intima or in the media.

1.1.5 Determination of Total Plasma Cholesterol Levels

Blood was collected via the tail vein from all mice after overnight fasting prior to initiation of the experiment, after 35 days feeding the different diets, and at time of death. Total plasma cholesterol levels were determined using the CHOD-PAP method (Boehringer Mannheim, Germany) as described previously (32).

1.1.6 Statistical Analysis

Results were analyzed by two-way analysis of variance with repeated measures and one-way analysis of variance with pairwise contrasts by Scheffé. Differences in expression of ICAM-1, VCAM-1 and CD11b-positive monocytes were analyzed with the nonparametric Kruskal-Wallis one-way Anova. Values of neointimal are and NI/M ratio were averaged for all groups and differences were analyzed with Kruskal-Wallis one-way Anova as well. Data shown are means±SEM. All tests were performed with SPSS for Windows Version 6.1.3.

1.2 Results 1.2.1 Cholesterol Levels and Manifestation of Atherosclerosis

Mean cholesterol concentrations in the study groups on day 35 were: Group 1 (control) 92±3 mg/dl, group 2 (atherogenic diet) 445±10 mg/dl and group 3 (atherogenic diet and $c^3Ado$) 410±19 mg/dl. Table 1 summarizes the characteristics of the different groups. Note the further increase from day 35 to day 65 during $c^3Ado$ treatment (group 3), which was statistically significant ($p<0.026$) and may be due to an interaction of 3-deazaadenosine with lipoprotein metabolism.

Figure 2:
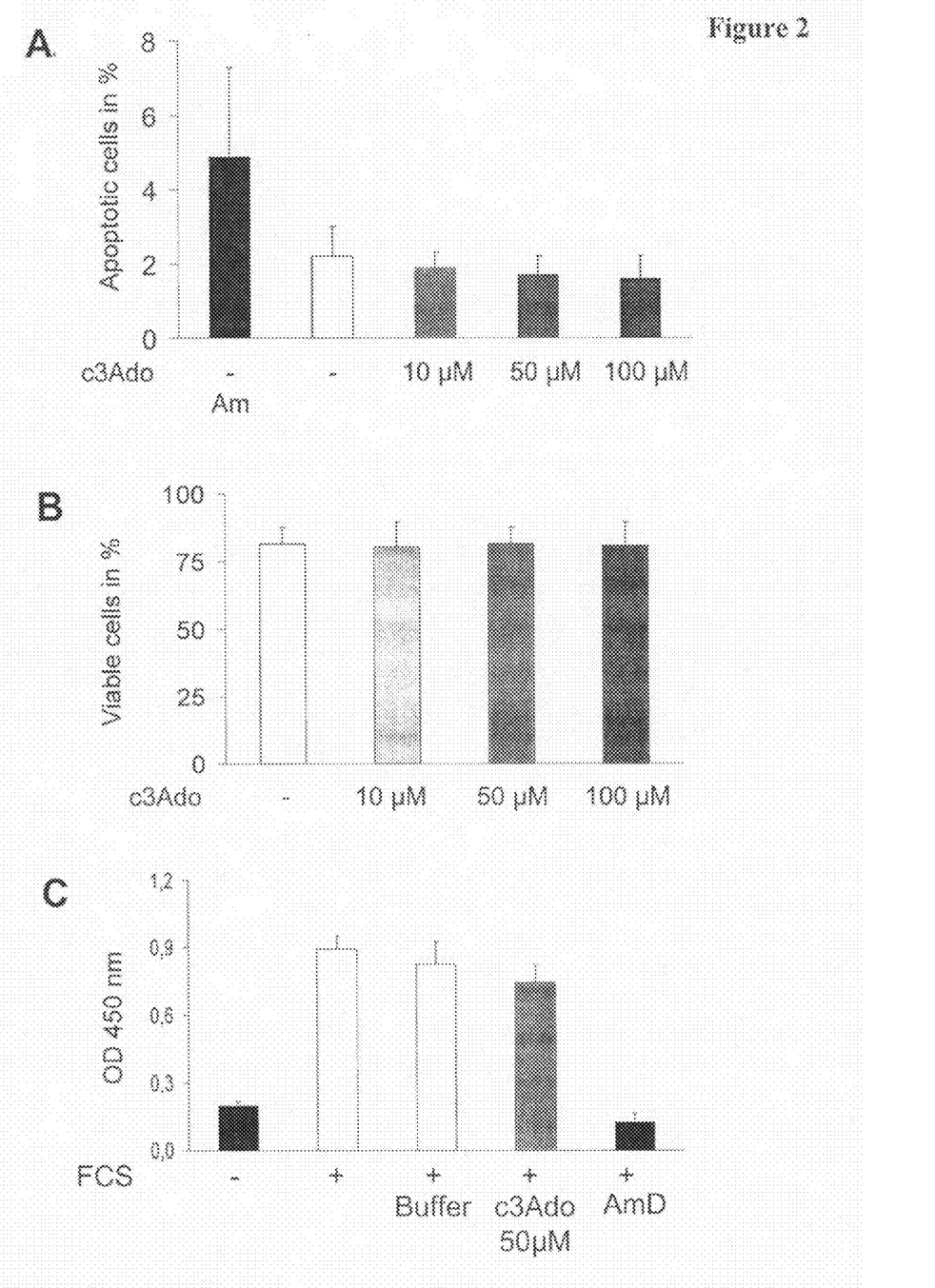
FIG. 2 Light micrograph of cross section of the aortic wall taken from female C57BL/6J mice fed with an atherogenic diet for 9 weeks. Note large lipid-rich, macrophage-rich fatty streak. Oil red O and hemalaun; original magnification×100; bar=5 μm.

In order to examine the aorta for fatty streak formation, 7 frozen sections of the ascending aorta per animal were quantified. Control mice did not show any atherosclerotic changes, whereas animals of study group 2 showed multiple lipid-containing lesions covering the vessel wall of the ascending aorta as demonstrated with oil red O staining (FIG. 2). The average number of lesions per animal in this group was 5.4±1.6 (range 0-14), and the percentage of the covered aortic lining was 3.4±2.8% (see Table 3). In contrast animals of group 3 which received $c^3Ado$ in addition to the atherogenic diet had no detectable lesions in the sections studied.

Figure 1:
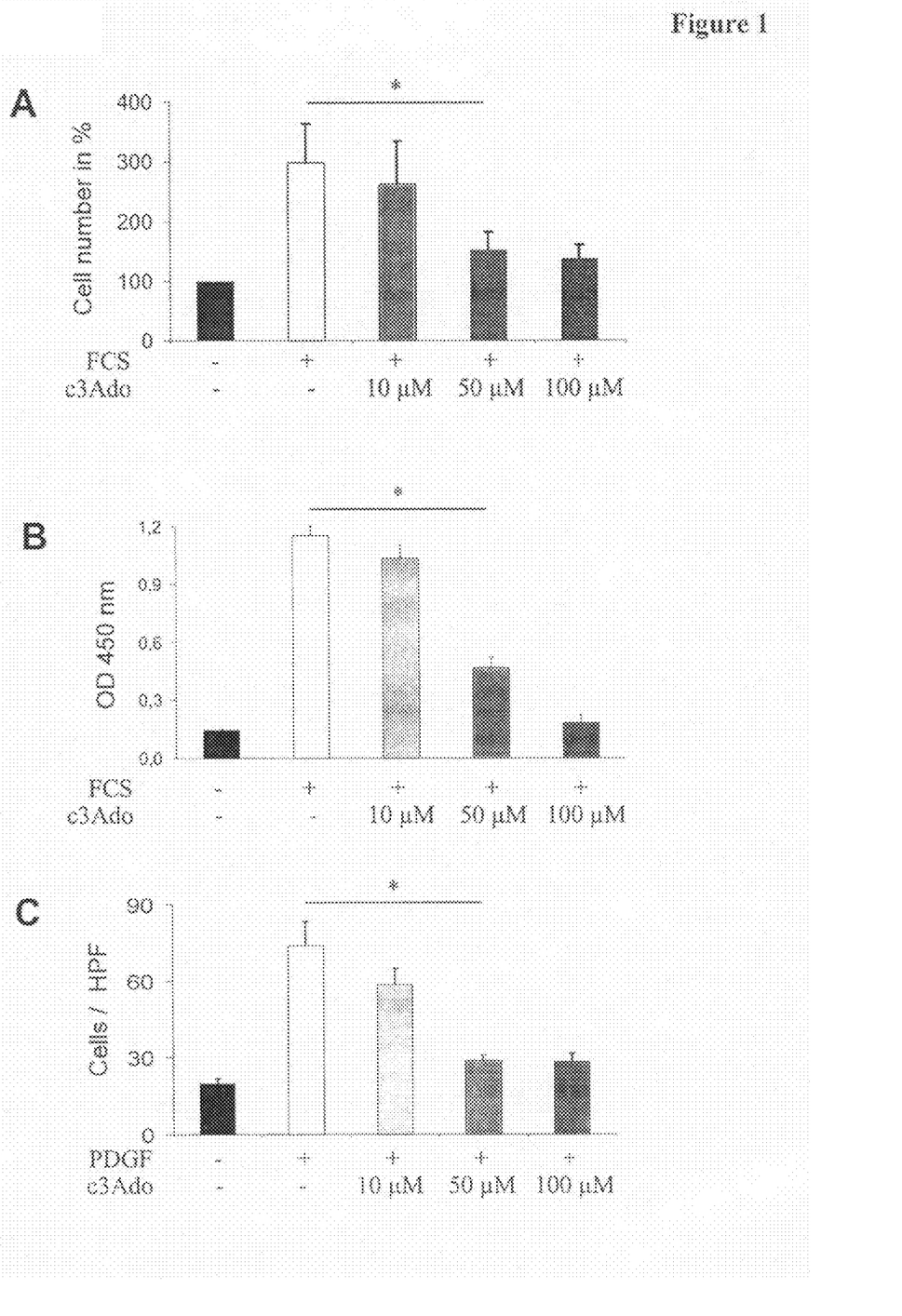
FIG. 1 Morphometric analysis of C57BL/J6 aortic sections. Bar graphs showing average neointimal to medial area ratio (NI/M) for control mice (n=9), mice on atherogenic diet (n=9), and mice on atherogenic diet and treatment with 3-deazaadenosine ($c^3$Ado) (n=9). Average NI/M was calculated for 3 histological sections per animal. Intimal/neointimal thickness as measured by NI/M was 94% lower in mice treated with $c^3$Ado compared to mice fed atherogenic diet without $c^3$Ado (p<0.001). There were no differences in NI/M between control and mice treated with $c^3$Ado. Values are means±SEM.
Figure 3:
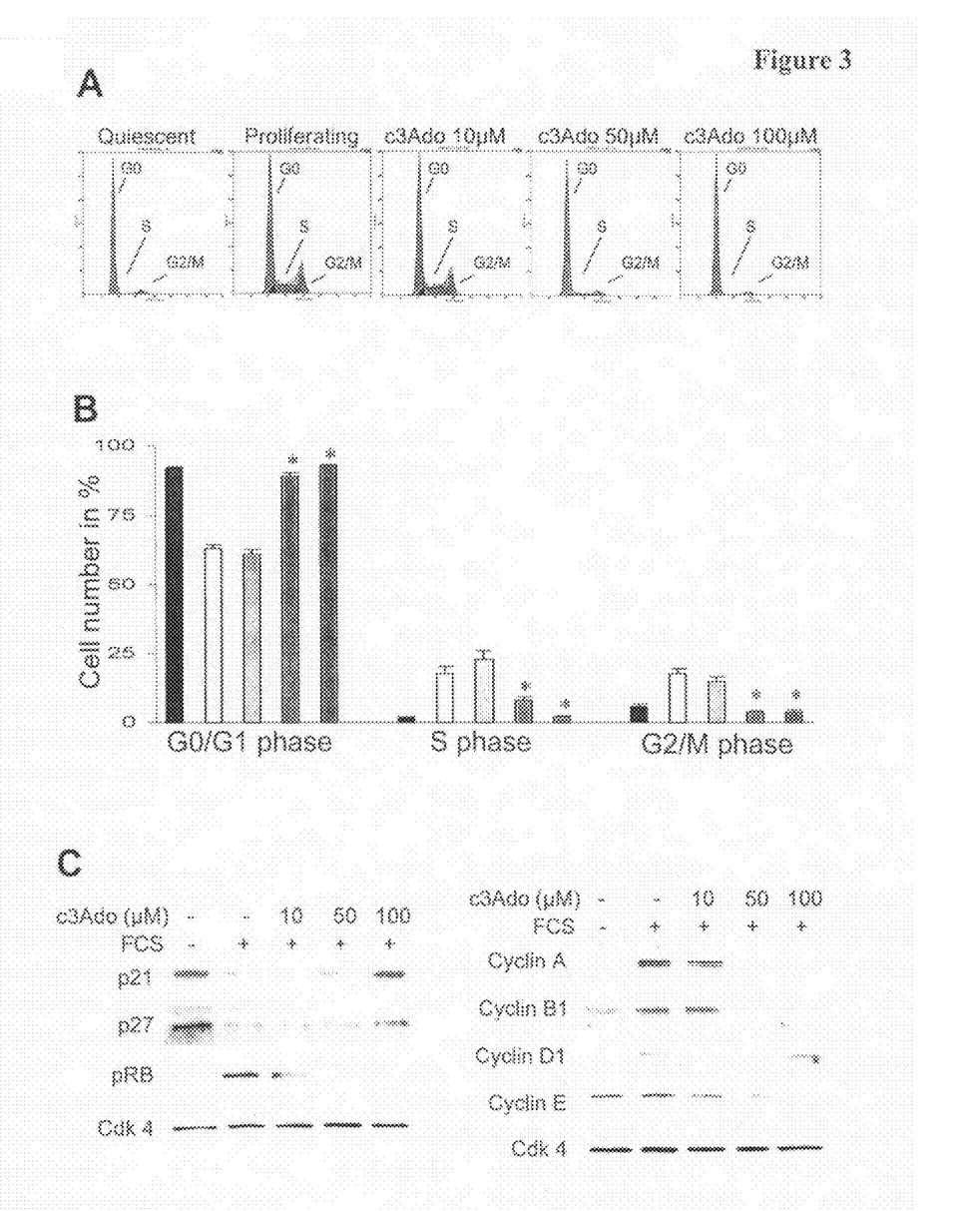

Mice in group 2 showed markedly enhanced neointimal proliferation when compared with animals of group 1 or group 3 (FIG. 3). Planimetric analysis of the intimal areas of the proximal ascending aorta demonstrated a strong increase of the neointima (450±775 $\mu m^2$) when compared to control mice (160±38 $\mu m^2$; $p<0.001$). Treatment with $c^3Ado$ in mice fed the atherogenic diet resulted in an inhibition of neointimal proliferation (125±32 $\mu m^2$; $p<0.001$). Neointimal thickness as measured by NI/M ratio was 94% lower in mice treated with $c^3Ado$ as compared to in mice with atherogenic diet alone (0.002±0.0004 vs. 0.033±0.005; $p<0.001$). Control mice showed the same NI/M ratio compared to the treatment group. In Table 3 and FIG. 1 these results are summarized.

1.2.2 Monocytes and Adhesion Molecules ICAM-1 and VCAM-1

Figure 5:
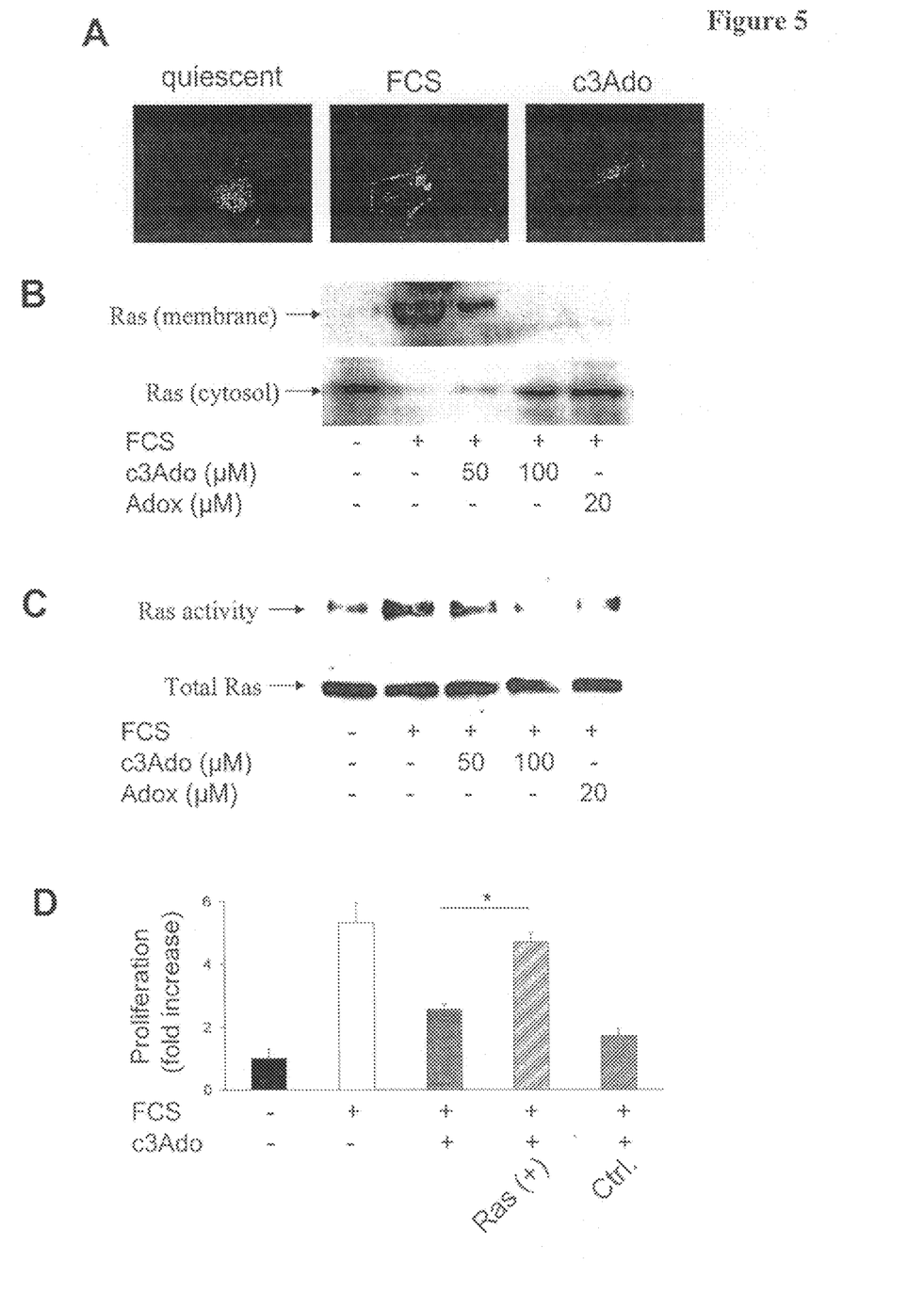
FIG. 5 High-magnification view of the aortic wall with an atherosclerotic intimal lesion and CD11b-positive monocyte (group 2, atherogenic diet). CD11b staining with monoclonal rat anti-mouse antibodies using the APAAP method and counterstaining with hemalaun. Original magnification×100; bar=5 μm.
Figure 6:
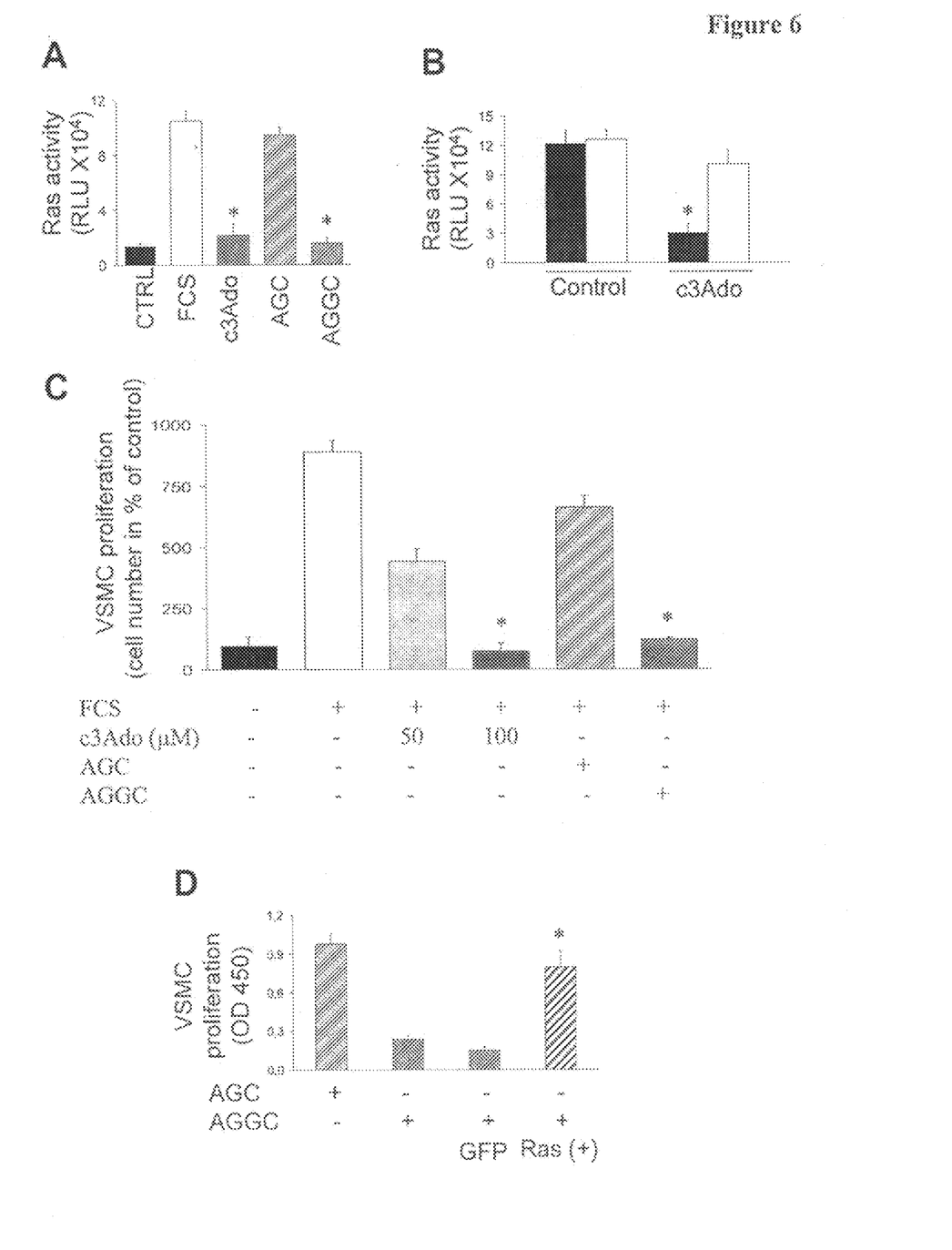
Figure 7:
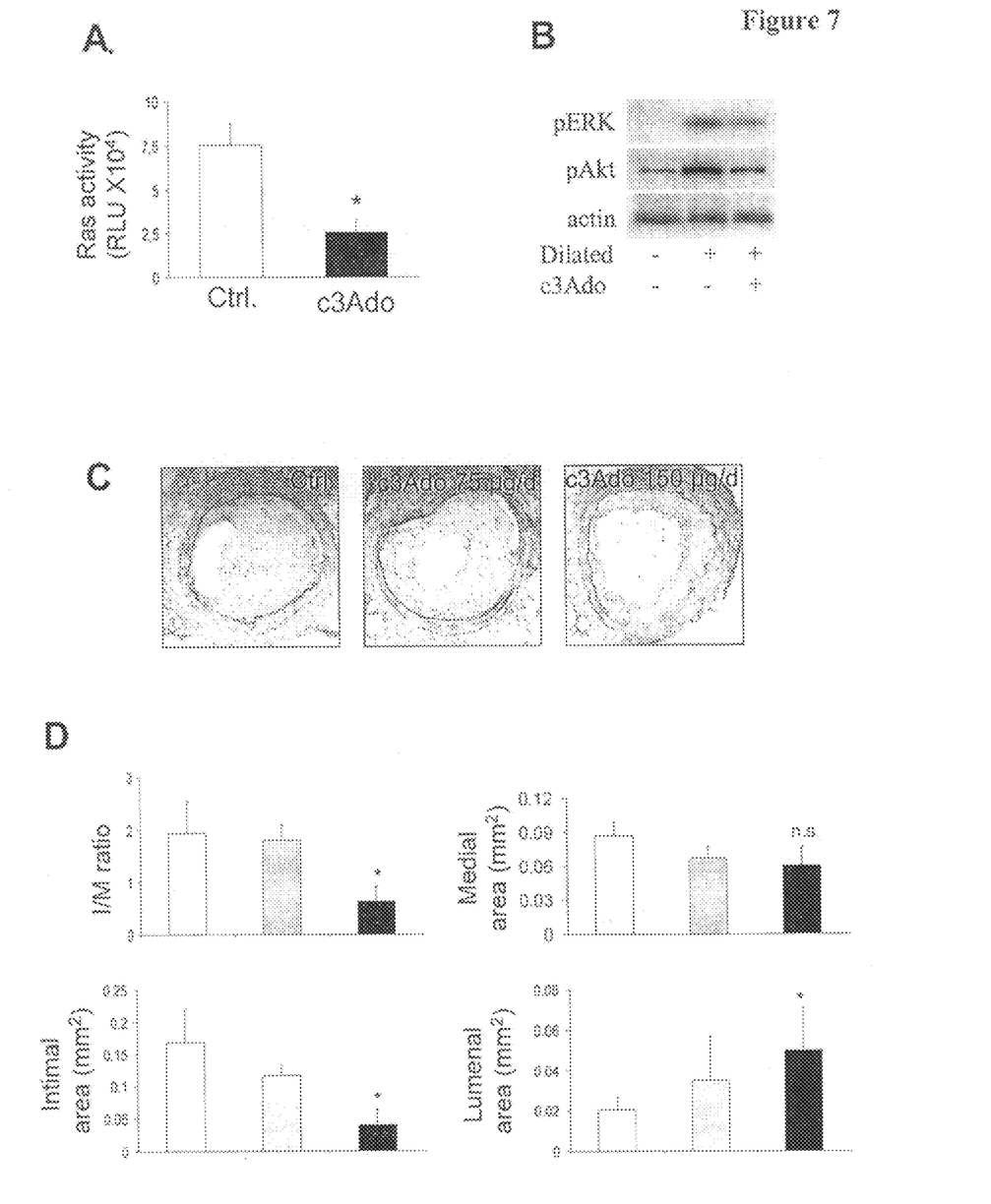
Figure 8:
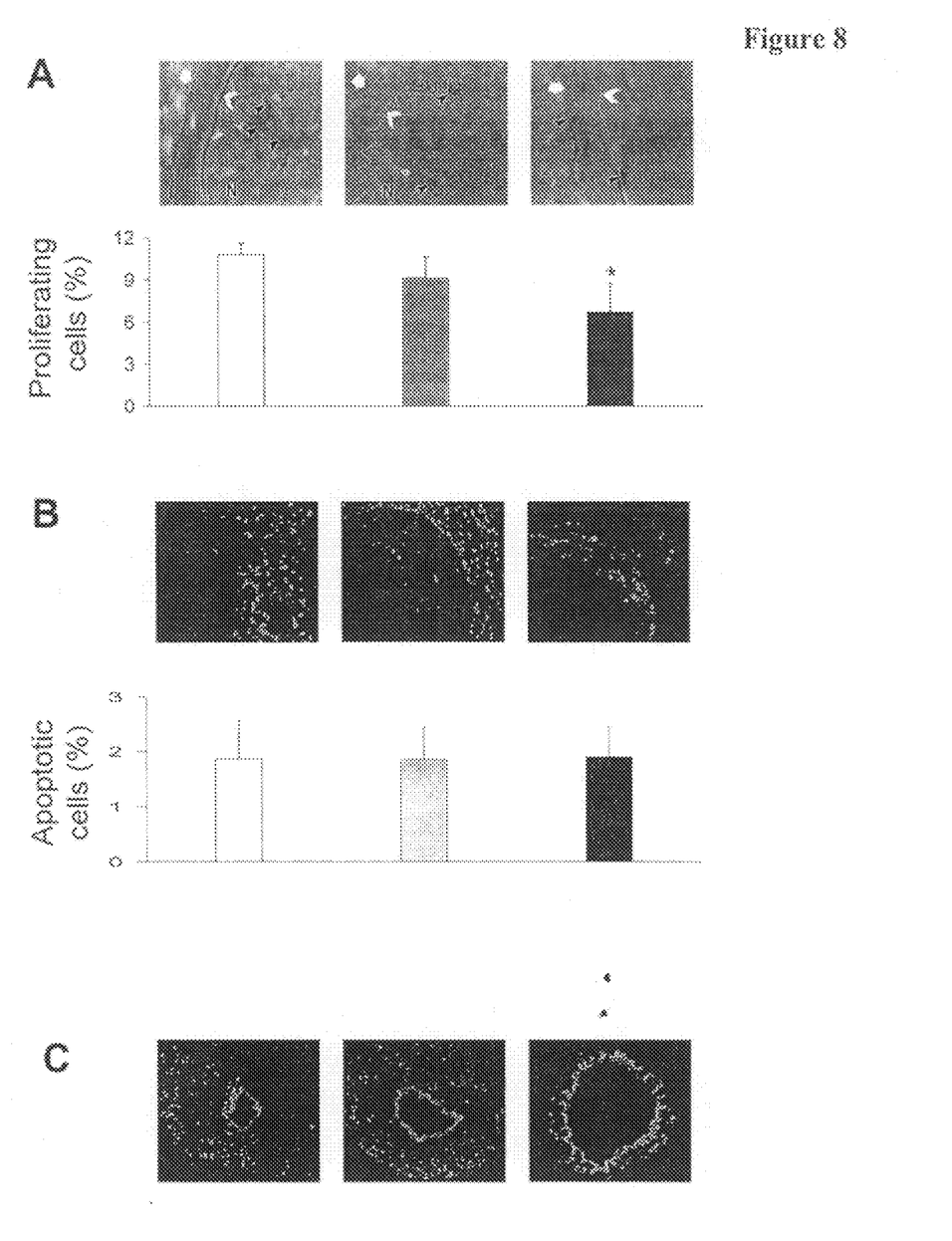

Animals fed the atherogenic diet showed CD11b-positive monocytic cells adhering to the endothelium and located within the intima of the aorta. Most of these cells were associated with atherosclerotic lesions (FIG. 5). In contrast, no monocytic cells within the intima and only a few adherent CD11b-positive cells on the luminal surface were detected in animals of group 3 which had received $c^3Ado$. In sections from control animals on standard diet no monocytes were present.

Figure 4:
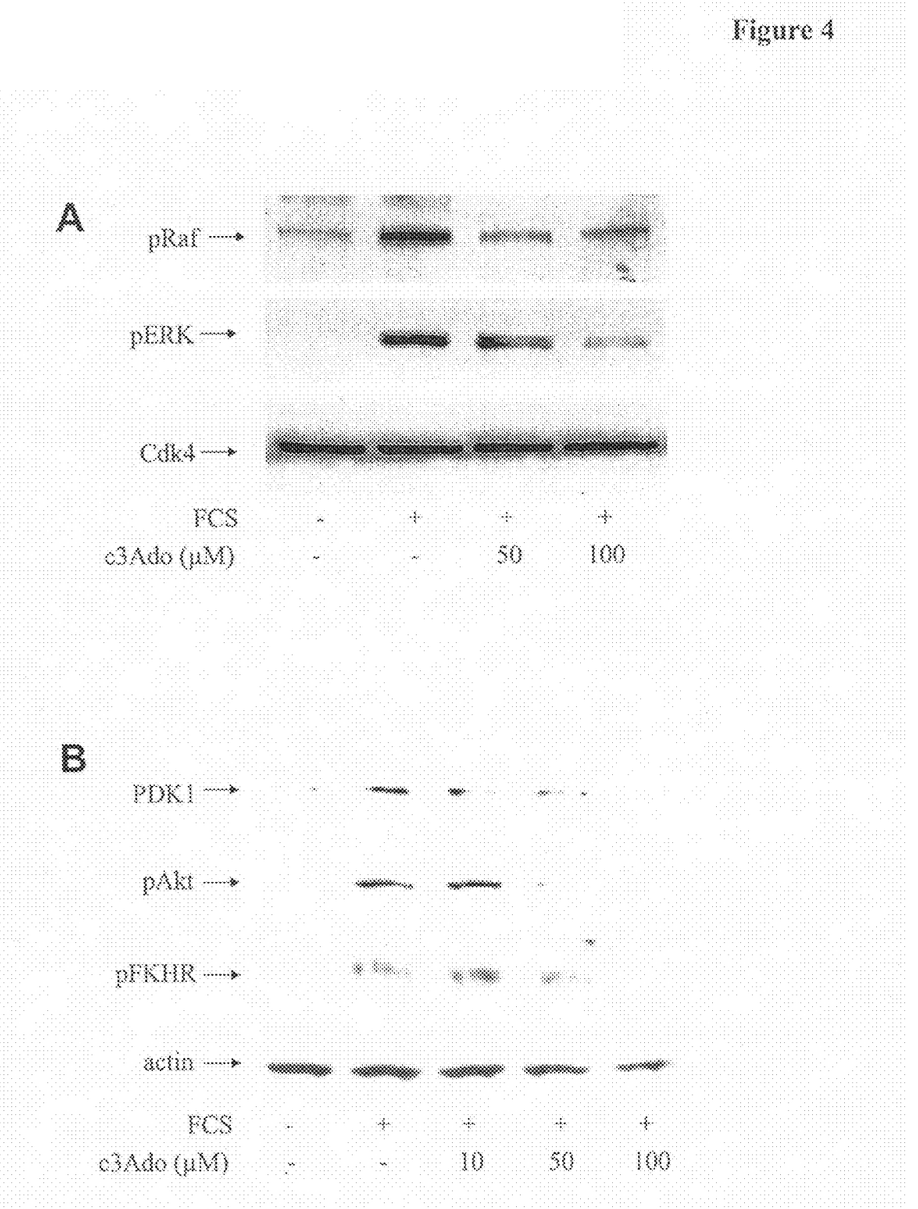

We furthermore investigated the regulation of adhesion molecules VCAM-1 and ICAM-1 which have both been suggested to be directly involved in atherosclerotic lesion formation. Immunohistological staining demonstrated intense endothelial expression of VCAM-1 and ICAM-1 in all analyzed frozen sections of the ascending aorta of mice on an atherogenic diet. Both adhesion molecules were abundantly expressed in lesions with extension toward non-involved regions. In striking contrast, the expression of VCAM-1 and ICAM-1 was completely absent in mice treated with $c^3$Ado as it was in control animals (FIG. 4). $c^3$Ado totally inhibited endothelial expression of both adhesion molecules. For a quantification of the images, refer to Table 2.

Tables

TABLE 1

Body Weight Developmant and Total Cholesterol Levels

| | Body weight day 0 (g) | Body weight day 65 (g) | Total cholesterol day 0 (mg/dl) | Total cholesterol day 35 (mg/dl) | Total cholesterol day 65 (mg/dl) |
|---|---|---|---|---|---|
| Group 1 (control) (n = 9) | 19.7 ± 0.2 | 23.1 ± 0.2 | 70 ± 5 | 92 ± 3 | 66 ± 4 |
| Group 2 (atherog. diet) (n = 9) | 19.3 ± 0.3 | 25.8 ± 0.2* | 59 ± 6 | 445 ± 10* | 434 ± 11* |
| Group 3 (atherog. diet + $c^3$Ado) (n = 9) | 19.6 ± 0.2 | 25.3 ± 0.2* | 70 ± 6 | 410 ± 19* | 475 ± 10* |
| | NS | | NS | | |

Values are expressed as means ± SEM. Differences between controls and groups 2 and 3 were statistically significant.
*p < 0.001, analyzed by two-way analysis of variance with repeated measures and one-way analysis of variance with pairwise contrast by Scheffé.
NS indicates not significant.

TABLE 2

Endothelial Expression of VCAM-1, ICAM-1 and Quantification of Endothelial and Intimal Monocytes.

| | VCAM-1 expression score | ICAM-1 expression score | Amount of intimal monocytes‡ | Amount of intimal monocytes‡ |
|---|---|---|---|---|
| Group 1 (control) (n = 9) | 1.1 ± 0.1 | 1.0 ± 0 | 0 ± 0 | 0 ± 0 |
| Group 2 (atherog.diet) | 3.3 ± 0.2* | 2.9 ± 0.3* | 3.6 ± 0.7† | 1.1 ± 0.2† |
| Group 3 (atherog.diet + $c^3$Ado) (n = 9) | 1.0 ± 0 | 1.0 ± 0 | 0.5 ± 0.2 | 0 ± 0 |

Differences between group 2 and group 3 were statistically significant. *p < 0.001 and † p = 0.004, analyzed by mean rank sums obtained with the Kruskal-Wallis test.
‡mean ± SEM per section scored out of 3 defined sections per animal.

TABLE 3

Quantification of Neointimal and Medial Areas, and Frequency of Fatty Streak Lesions

| | Neointimal Area† ($\mu m^2$) | Medial Area† ($\mu m^2$) | NI/M Ratio | Number of lesions‡ |
|---|---|---|---|---|
| Group 1 (control) (n = 9) | 0.16 ± 0.04 × $10^3$ | 60.6 ± 2.1 × $10^3$ | 0.003 ± 0.0006 | 0 ± 0 |
| Group 2 (atherog. diet) (n = 9) | 4.5 ± 0.8 × $10^{3*}$ | 135.2 ± 5.8 × $10^{3*}$ | 0.033 ± 0.005 | 5.4 ± 1.6* |
| Group 3 (atherog. diet + $c^3$Ado) (n = 9) | 0.13 ± 0.03 × $10^3$ | 62.7 ± 2.5 × $10^3$ | 0.002 ± 0.0004 | 0 ± 0 |

†Diffences were statistically relevant. *p < 0.001, analyzed by mean rank sums obtained with the Kruskal-Wallis test.
‡mean ± SEM determined out of 3 sections per animal.
mean ± SEM calculated from 7 sections per animal.

EXAMPLE 2

Blocking of Heart Allograft Rejection and Heart Allograft Atherosclerosis

Materials and Methods 2.1.1 Animals and Experimental Design

3-Deazaadenosine was orally administered by mixing into the regular food at a final concentration of 0.04 mg/g, according to a daily oral dose of 10 mg/kg c3Ado per animal, in addition to or in absence of cyclosporine (0.2 mg/kg body weight) to Lewis rats which received heterotopically transplanted hearts from Fisher rats. For a third control group, only cyclosporine was administered daily to the other allograft recipients. All animals got a standard diet over the whole study period. Allografts were harvested on day 120, cardiac graft beat was assessed by daily palpation, and the complete cessation of the graft beat was interpreted as rejection. All of the rats accepted cardiac allografts without any further treatment for the duration of observation.

2.1.2 Immunohistochemical Analysis

For immunohistochemical analysis of VCAM-1 and ICAM-1, two complete transverse sections of the transplanted heart approximately 3 mm in thickness were obtained and stored in optimum cutting temperature compound. Serial sections were cut and dipped in cold acetone for 10 minutes. The staining procedures were performed as described previously. The expression of the adhesion molecules was scored on the basis of endothelial cells and smooth muscle cells of epicardial arteries and intramyocardial ateriolies. Analysis was done semiquantitatively by scoring the intensity of the staining and counting of the number of stained cells.

2.1.3 Definition of Graft Vasculopathy

Definition of graft vasculopathy was performed as follows: Blood vessels that had a well-defined smooth muscle cell layer and internal elastica lamina in the vascular wall were identified as traceable arteries. Every complete cross-section of the traceable arteries was calculated. The sections were reviewed by two independent reviewers masked to the status of the slides, and histologic changes were assessed semiquantitatively. The changes of intimal thickening were scored as mild (score 1, <25% occlusion of the lumen) when the intima was readily discernible, or as moderate (score 2, 25-50% occlusion) to severe (score 3, >50% occlusion).

2.2 Results

2.2.1 Graft Survival and Complications

The isografts and allografts in rats that received 3-deazaadenosine or cyclosporine or both drugs together kept beating for the duration of observation. Strength of the allograft beat was comparable to that of isografts. No complications occurred as a result of 3-deaza therapy. In mice receiving 3-deaza grafts were completely free from rejection whereas animals receiving cyclosporine alone mild rejection was seen.

Therefore, 3-deazaadenosine significantly reduced rejection of transplanted hearts with the same (or better) efficacy as the known immunosuppressive drug cyclosporine.

2.2.2 Graft Atherosclerosis

Native hearts and isografts showed no intimal thickening in coronary arteries. In the group of rats that received cyclosporine the intramyocardial and epicardial arteries showed significant intimal thickening and one third of the vessels were nearly occluded after 120 days. In the group of rats that received 3-deazaadenosine there was almost no arterial intimal thickening.

Therefore, 3-deazaadenosine significantly inhibited graft atherosclerosis in the transplanted hearts.

2.2.3 Expression of Adhesion Molecules ICAM-1 and VCAM-1

Isografts and native hearts were equally free from ICAM-1 and VCAM-1 expression. In contrast, these molecules were extensively upregulated in the neointima of transplanted hearts receiving cyclosporine alone. Conversely, there was almost no expression of ICAM-1 and VCAM-1 in rats which received 3-deazaadenosine.

Therefore, 3-deazaadenosine blocks the expression of ICAM-1 and VCAM-1 in the intima of coronary arteries from transplanted hearts.

REFERENCES

1. Ross, Nature 1993, 362:801-9
2. Alexander, N. Engl. J. Med. 1994, 331:468-9
3. Entmann and Ballantyne, Circulation 1993, 22:800-3
4. Springer, Cell 1994, 76:301-314
5. Steinberg and Witztum, JAMA 1990, 264:3047-3052
6. Jang et al., J. Am. Coll. Cardiol. 1994, 24:1597-1601
7. Poston et al., Am. J. Pathol. 1992, 140:665-673
8. Cybulsky et al., Science 1991, 251:788-91
9. Li et al., Atheroscler. Thromb. 1993, 13:197-204
10. Richardson et al., Arterioscler. Thromb. 1994, 14; 760-769
11. Qiao et al., Arterioscler. Thromb. 1994, 14:1480-1497
12. van der Wal et al., Am. J. Pathol. 1992, 141:1427-1433
13. O'Brien et al. J. Clin. Invest. 1993, 92:945-951
14. Nageh at al., Arterioscler. Thromb. Vasc. Biol. 1997, 17:1517-1520
15. Aksamit et al., J. Biol. Chem. 1982, 257:621-625
16. Aksamit et al., J. Biol. Chem. 1983, 258:20-23
17. Garcia-Castro et al., J. Biol. Chem. 1983, 4345-4349
18. Medzihradsky, J. Immunol. 1984, 133:946-949
19. Jurgensen et al., J. Immunol. 1990, 144:653-661
20. Chiang: In Biological Methylation and Drug Design (Borchardt R T, Creveling C R, Ueland P M, eds.), Humana Press, Clifton, N.J. 1986:239-251
21. Cantoni: in Biological Methylation and Drug Design (Borchardt R T, Creveling C R, Ueland P M, eds.), Humana Press, Clifton, N.J. 1986:227-238
22. Sung and Silverstein, J. Biol. Chem. 1985, 260:546-554
23. Zimmermann et al., J. Biol. Chem. 1984, 259:1122-1126
24. Zimmermann et al.: in Biological Methylation and Drug Design (Borchardt R T, Creveling C R, Ueland P M, eds.), Humana Press, Clifton, N.J. 1986:417-426
25. Smith et al., Int. J. Tiss. Reac. 1991, 13:1-18
26. Flexner et al., Lancet 1992, 339:438 (letter)
27. Paigen et al. Atherosclerosis 1985, 57:65-73
28. Paigen et al., Proc. Natl. Acad. Sci. USA 1987, 84:3763-3767
29. Paigen et al., Atherosclerosis 1987, 68:231-240
30. Ishida and Paigen: in Atherosclerosis in the Mouse. Genetic Factors in Atherosclerosis: Approaches and Model Systems. 1989, Basel Switzerland, Karger, pp. 189-222
31. Emeson and Shen, Am. J. Pathol. 1993, 142:1905-1915
32. Kattermann et al., J. Clin. Chem. Clin. Biochem. 1984, 22:245-251
33. Lin et al., Atherosclerosis 1995, 115:85-88
34. Berrity, Am. J. Pathol. 1981, 103:181-190
35. Munro and Cotran, Lab. Invest. 1988, 58:249-261
36. Ross and Fuster, Atherosclerosis and Coronary Artery Disease. Edited by Fuster V, Ross R and Topol E J. Philadelphia, Lippincott-Raven Publisher, 1996, pp. 511-537
37. Cybulsky et al., FASEB J. 1992, 6:1030A
38. Davies et al., J. Pathol. 1993, 171:223-229
39. Leonard et al., Biochem. Biophys. Res. Commun. 1974, 84:102-110
40. Shankar et al., J. Biol. Chem. 1992, 267:9376-9382

The invention claimed is:

1. A method of treating in-stent restenosis, a reperfusion injury, an infectious coronary syndrome, an inflammatory coronary syndrome, dilated cardiomyopathy, viral myocarditis or a reperfusion injury comprising implanting a stent coated with 3-deazaadenosine or an analog of 3-deazaadenosine selected from the group consisting of a salt of 3-deazaadenosine and a precursor of 3-deazaadenosine which degrades to 3-deazaadenosine in a body under physiological conditions in a patient in need thereof.

2. The method of claim 1, wherein in-stent restenosis is treated.

3. A method of treating reperfusion injuries comprising implanting a stent coated with 3-deazaadenosine or an analog of 3-deazaadenosine selected from the group consisting of a salt of 3-deazaadenosine and a precursor of 3-deazaadenosine which degrades to 3-deazaadenosine in a body under physiological conditions in a patient in need thereof.

4. A method of treating an infectious coronary syndrome comprising implanting a stent coated with 3-deazaadenosine or an analog of 3-deazaadenosine selected from the group consisting of a salt of 3-deazaadenosine and a precursor of 3-deazaadenosine which degrades to 3-deazaadenosine in a body under physiological conditions in a patient in need thereof.

5. A method of treating an infectious coronary syndrome comprising implanting a stent coated with 3-deazaadenosine or an analog of 3-deazaadenosine selected from the group consisting of a salt of 3-deazaadenosine and a precursor of 3-deazaadenosine which degrades to 3-deazaadenosine in a body under physiological conditions in a patient in need thereof, wherein said analog of deazaadenosine is selected from the group consisting of 3-deazaadenosine-3'-monophosphoric acid, 3-deazaadenosine-3'5'-cyclophosphate and 3-deazaadenosine-5'-diphosphoric acid.

6. A method of treating an inflammatory coronary syndrome comprising implanting a stent coated with 3-deazaadenosine or an analog of 3-deazaadenosine selected from the group consisting of a salt of 3-deazaadenosine and a precursor of 3-deazaadenosine which degrades to 3-deazaadenosine in a body under physiological conditions in a patient in need thereof.

7. A method of preventing an inflammatory coronary syndrome comprising implanting a stent coated with 3-deazaadenosine or an analog of 3-deazaadenosine selected from the group consisting of a salt of 3-deazaadenosine and a precursor of 3-deazaadenosine which degrades to 3-deazaadenosine in a body under physiological conditions in a patient in need thereof.

8. A method of treating dilated cardiomyopathy comprising implanting a stent coated with 3-deazaadenosine or an analog of 3-deazaadenosine selected from the group consisting of a salt of 3-deazaadenosine and a precursor of 3-deazaadenosine which degrades to 3-deazaadenosine in a body under physiological conditions in a patient in need thereof.

9. A method of treating dilated cardiomyopathy comprising implanting a stent coated with 3-deazaadenosine or an analog of 3-deazaadenosine selected from the group consisting of a salt of 3-deazaadenosine and a precursor of 3-deazaadenosine which degrades to 3-deazaadenosine in a body under physiological conditions in a patient in need thereof, wherein said analog of deazaadenosine is selected from the group consisting of 3-deazaadenosine-3'-monophosphoric acid, 3-deazaadenosine-3'5'-cyclophosphate and 3-deazaadenosine-5'-diphosphoric acid.

10. A method of treating viral myocarditis by implanting a stent coated with 3-deazaadenosine or an analog of 3-deazaadenosine selected from the group consisting of a salt of 3-deazaadenosine and a precursor of 3-deazaadenosine which degrades to 3-deazaadenosine in a body under physiological conditions in a patient in need thereof.

11. A method of treating viral myocarditis by implanting a stent coated with 3-deazaadenosine or an analog of 3-deazaadenosine selected from the group consisting of a salt of 3-deazaadenosine and a precursor of 3-deazaadenosine which degrades to 3-deazaadenosine in a body under physiological conditions in a patient in need thereof, wherein said analog of deazaadenosine is selected from the group consisting of 3-deazaadenosine-3'-monophosphoric acid, 3-deazaadenosine-3'5'-cyclophosphate and 3-deazaadenosine-5'-diphosphoric acid.

12. A method according to claim 1, wherein the method comprises treating in-stent restenosis, an inflammatory coronary syndrome, dilated cardiomyopathy, or viral myocarditis.

13. A method according to claim 1, wherein the method comprises treating in-stent restenosis, a reperfusion injury, an inflammatory coronary syndrome, or dilated cardiomyopathy.

14. The method of claim 12, wherein in-stent restonosis or viral myocarditis is treated.

15. The method of claim 13, wherein a reperfusion injury or an inflammatory coronary syndrome is treated.

* * * * *